(12) United States Patent
Fujihara et al.

(10) Patent No.: US 6,730,302 B1
(45) Date of Patent: May 4, 2004

(54) INTRACELLULAR TARGETED DELIVERY OF COMPOUNDS BY 70 KD HEAT SHOCK PROTEIN

(75) Inventors: Sheri M. Fujihara, Lawrenceville, NJ (US); Steven G. Nadler, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/440,967

(22) Filed: Nov. 16, 1999

Related U.S. Application Data

(60) Provisional application No. 60/109,872, filed on Nov. 24, 1998.

(51) Int. Cl.$^7$ .................. A61K 39/385; A61K 38/17
(52) U.S. Cl. ................. 424/192.1; 424/193.1; 424/195.11; 512/2; 512/12
(58) Field of Search .................. 514/2, 12; 424/192.1, 424/193.1, 195.11

(56) References Cited

U.S. PATENT DOCUMENTS

| | | | | |
|---|---|---|---|---|
| 5,985,270 A | * | 11/1999 | Srivastava | 424/184.1 |
| 6,017,544 A | * | 1/2000 | Srivastava | 42/277.1 |
| 6,335,183 B1 | * | 1/2002 | Young et al. | 435/69.7 |

FOREIGN PATENT DOCUMENTS

| | | |
|---|---|---|
| WO | WO94/29459 | 12/1994 |

OTHER PUBLICATIONS

Lamian et al. Evidence for the existence of a novel mechanism for the nuclear import of Hsc70. Experimental Cell Research 228 : 84–91. (1996).*
Guzhova et al. Effects of exogenous stress protein 70 on the functional properties of human promonocytes through binding to cell surface and internalization. Cell stress and Chaperones 3(1): 67–77. (1998).*
Fujihara et al. (1999) EMBO, 18:2:411–419.
Milner et al. (1990) Immunogenetics 32:242–251.
Elliott et al. (1997) Cell 88:223–233.
Vives et al. (1997) J. Biol. Chem. 272:16010–16017.
Hawiger (1997) Curr. Opin. Immun. 9:189–194.
Pooga et al. (1998) FASEB J. 12:67–77.
Phelan et al. (1998) Nature Biotechnology 16:440–443.
Fawell et al. (1994) Proc.Natl.Acad.Sci 91:664–668.
Rojas et al. (1998) Nature Biotechnology 16:370–375.
Rom´´n et al. (1996) Immunology 88:487–492.
Suzue et al. (1996) J.Immunol 156:873–879.
Udono et al. (1993) J.Exp.Med. 178:1391–1396.
Hightower et al. (1989) J.Cell.Physiol. 138:257–266.
Meyer et al. (1991) PNAS 88:966–970.
Multhoff et al. (1996) Cell Stress & Chaperones 1:167–176.
Shi et al. (1998) Genes Dev. 12:654–666.
Meheswaran et al. (1998) Genes Dev. 12:1108–1120.
Demand et al. (1998) Mol.Cell.Biol. 18:2023–2028.
Lasunskaia et al. (1997) Apoptosis 2:156–163.
Blachere et al. (1997) J.Exp.Med. 187:685–691.
Ciupitu et al. (1998) J.Exp.Med. 187:685–691.
Fujihara et al. (1998) Biochem.Pharm. 56:157–161.
Fujita et al. (1992) Genes Dev. 6:775–787.
Manara et al. (1993) Blood 82:2865–2871.
Vanbuskirk et al. (1989) J.Exp.Med. 170:1799–1809.
Takakura et al. (1996) Pharm.Research 13:820–831.
Margulis et al. (1991) Diabetes 40:1418–1422.
Dang et al. (1989) Journal.Biol.Chem 264:18019–18023.
Perkins et al. (1992) 89:1529–1533.
Leclair et al. (1992) Proceedings of Natl.Acad.Sciences 89:8145–8149.
Johnson et al. (1993) 29A:807–812.
Fix (1996) Pharm.Research 13:1760–1764.

* cited by examiner

*Primary Examiner*—Gabriele Bugaisky
(74) *Attorney, Agent, or Firm*—Audrey F. Sher; Christopher A. Klein

(57) ABSTRACT

The present invention provides a carrier for the delivery of molecules with biological function into both cellular and nuclear compartments. The carrier disclosed is heat shock protein 70 ("Hsp70"), or a fragment of Hsp70 as described herein, as a vehicle for directed, noninvasive delivery of molecules, such as proteins, peptides, or DNA, that may modulate cellular activity. The present invention also encompasses the use of Hsp70, or a fragment thereof, to modulate cellular activity, preferably to modulate nuclear activity in a cell or cells.

35 Claims, 8 Drawing Sheets

SEQUENCE LISTING

```
<160> NUMBER OF SEQ ID NOS: 5

<210> SEQ ID NO 1
<211> LENGTH: 373
<212> TYPE: PRT
<213> ORGANISM: Homo Sapien

<400> SEQUENCE: 1

Leu Pro Thr Asp Gly Pro Tyr Leu Gln Ile Leu Glu Gln Pro Lys Gln
1               5                   10                  15

Arg Gly Phe Arg Phe Arg Tyr Val Cys Glu Gly Pro Ser His Gly Gly
            20                  25                  30
```

Leu Pro Gly Ala Ser Ser Glu Lys Asn Lys Ser Tyr Pro Gln Val
            35                  40                  45

Lys Ile Cys Asn Tyr Val Gly Pro Ala Lys Val Ile Val Gln Leu Val
 50                  55                  60

Thr Asn Gly Lys Asn Ile His Leu His Ala His Ser Leu Val Gly Lys
65                   70                  75                  80

His Cys Glu Asp Gly Ile Cys Thr Val Thr Ala Gly Pro Lys Asp Met
                    85                  90                  95

Val Val Gly Phe Ala Asn Leu Gly Ile Leu His Val Thr Lys Lys Lys
                100                 105                 110

Val Phe Glu Thr Leu Glu Ala Arg Met Thr Glu Ala Cys Ile Arg Gly
                115                 120                 125

Tyr Asn Pro Gly Leu Leu Val His Pro Asp Leu Ala Tyr Leu Gln Ala
            130                 135                 140

Glu Gly Gly Gly Asp Arg Gln Leu Gly Asp Arg Glu Lys Glu Leu Ile
145                 150                 155                 160

Arg Gln Ala Ala Leu Gln Gln Thr Lys Glu Met Asp Leu Ser Val Val
                165                 170                 175

Arg Leu Met Phe Thr Ala Phe Leu Pro Asp Ser Thr Gly Ser Phe Thr
                180                 185                 190

Arg Arg Leu Glu Pro Val Val Ser Asp Ala Ile Tyr Asp Ser Lys Ala
            195                 200                 205

Pro Asn Ala Ser Asn Leu Lys Ile Val Arg Met Asp Arg Thr Ala Gly
        210                 215                 220

Cys Val Thr Gly Gly Glu Glu Ile Tyr Leu Leu Cys Asp Lys Val Gln
225                 230                 235                 240

Lys Asp Asp Ile Gln Ile Arg Phe Tyr Glu Glu Glu Asn Gly Gly
                245                 250                 255

Val Trp Glu Gly Phe Gly Asp Phe Ser Pro Thr Asp Val His Arg Gln
            260                 265                 270

Phe Ala Ile Val Phe Lys Thr Pro Lys Tyr Lys Asp Ile Asn Ile Thr
        275                 280                 285

Lys Pro Ala Ser Val Phe Val Gln Leu Arg Arg Lys Ser Asp Leu Glu
        290                 295                 300

Thr Ser Glu Pro Lys Pro Phe Leu Tyr Tyr Pro Glu Ile Lys Asp Lys
305                 310                 315                 320

Glu Glu Val Gln Arg Lys Arg Gln Lys Leu Met Pro Asn Phe Ser Asp
                325                 330                 335

Ser Phe Gly Gly Gly Ser Gly Ala Gly Ala Gly Gly Gly Met Phe
            340                 345                 350

Gly Ser Gly Gly Gly Gly Gly Thr Gly Ser Thr Gly Pro Gly Tyr
        355                 360                 365

Ser Phe Pro His Tyr
    370

<210> SEQ ID NO 2
<211> LENGTH: 244
<212> TYPE: PRT
<213> ORGANISM: Homo Sapien

<400> SEQUENCE: 2

Pro Leu Ser Leu Gly Leu Glu Thr Ala Gly Gly Val Met Thr Ala Leu
1               5                   10                  15

Ile Lys Arg Asn Ser Thr Ile Pro Thr Lys Gln Thr Gln Ile Phe Thr
            20                  25                  30

-continued

```
Thr Tyr Ser Asp Asn Gln Pro Gly Val Leu Ile Gln Val Tyr Glu Gly
            35                  40                  45
Glu Arg Ala Met Thr Lys Asp Asn Asn Leu Leu Gly Arg Phe Glu Leu
     50                  55                  60
Ser Gly Ile Pro Pro Ala Pro Arg Gly Val Pro Gln Ile Glu Val Thr
 65                  70                  75                  80
Phe Asp Ile Asp Ala Asn Gly Ile Leu Asn Val Thr Ala Thr Asp Lys
                    85                  90                  95
Ser Thr Gly Lys Ala Asn Lys Ile Thr Ile Thr Asn Asp Lys Gly Arg
                100                 105                 110
Leu Ser Lys Glu Glu Ile Glu Arg Met Val Gln Glu Ala Glu Lys Tyr
            115                 120                 125
Lys Ala Glu Asp Glu Val Gln Arg Glu Arg Val Ser Ala Lys Asn Ala
    130                 135                 140
Leu Glu Ser Tyr Ala Phe Asn Met Lys Ser Ala Val Glu Asp Glu Gly
145                 150                 155                 160
Leu Lys Gly Lys Ile Ser Glu Ala Asp Lys Lys Val Leu Asp Lys
                165                 170                 175
Cys Gln Glu Val Ile Ser Trp Leu Asp Ala Asn Thr Leu Ala Glu Lys
                180                 185                 190
Asp Glu Phe Glu His Lys Arg Lys Glu Leu Glu Gln Val Cys Asn Pro
            195                 200                 205
Ile Ile Ser Gly Leu Tyr Gln Gly Ala Gly Gly Pro Gly Pro Gly Gly
        210                 215                 220
Phe Gly Ala Gln Gly Pro Lys Gly Gly Ser Gly Ser Gly Pro Thr Ile
225                 230                 235                 240
Glu Glu Val Asp

<210> SEQ ID NO 3
<211> LENGTH: 92
<212> TYPE: PRT
<213> ORGANISM: Homo Sapien

<400> SEQUENCE: 3

Lys Ser Ala Val Glu Asp Glu Gly Leu Lys Gly Lys Ile Ser Glu Ala
 1               5                  10                  15
Asp Lys Lys Val Leu Asp Lys Cys Gln Glu Val Ile Ser Trp Leu
                20                  25                  30
Asp Ala Asn Thr Leu Ala Glu Lys Asp Glu Phe Glu His Lys Arg Lys
            35                  40                  45
Glu Leu Glu Gln Val Cys Asn Pro Ile Ile Ser Gly Leu Tyr Gln Gly
     50                  55                  60
Ala Gly Gly Pro Gly Pro Gly Gly Phe Gly Ala Gln Gly Pro Lys Gly
 65                  70                  75                  80
Gly Ser Gly Ser Gly Pro Thr Ile Glu Glu Val Asp
                    85                  90

<210> SEQ ID NO 4
<211> LENGTH: 35
<212> TYPE: DNA
<213> ORGANISM: Homo Sapien

<400> SEQUENCE: 4
gatccgaggg gactttccgc tggggacttt ccagg                              35
```

-continued

```
<210> SEQ ID NO 5
<211> LENGTH: 22
<212> TYPE: DNA
<213> ORGANISM: Homo Sapien

<400> SEQUENCE: 5
tgtcgaatgc aaatcactag aa                                              22
```

INTRACELLULAR TARGETED DELIVERY OF COMPOUNDS BY 70 KD HEAT SHOCK PROTEIN

This invention claims priority from provisional U.S. application Serial No. 60/109,872, filed Nov. 24, 1998, which is incorporated herein by reference in its entirety.

FIELD OF THE INVENTION

The present invention relates to the intracellular delivery, preferably the intranuclear delivery, of compounds using the heat shock protein Hsp70.

BACKGROUND OF THE INVENTION

Heat shock proteins ("Hsps") are a family of molecular chaperone proteins which have long been known to play essential roles in a multitude of intra- and intercellular processes, including protein synthesis and folding, vesicular trafficking, and antigen processing and presentation. Hsps are among the most highly conserved proteins known, and carry out many of their regulatory activities via protein—protein interactions. Hsp70 is one member of the heat shock protein family. (Milner, C. M. and Campbell, R. D. *Immunogenetics* 32:242–251 (1990), Genbank Accession No. M59828). One of the most well characterized functions of Hsp70 is to assist in the translocation of proteins across intracellular membranes into different compartments of the cell.

Intracellular transport activity has been reported for viral proteins such as the HSV-1 structural protein VP22 (Elliott, et. al., (1997) *Cell* 88:223–233) and the HIV Tat protein (Vives, et. al., (1997) *J. Biol. Chem.* 272:16010–16017), as well as peptide sequences derived from Antennapedia homeodomain, fibroblast growth factor (Hawiger, (1997) *Curr. Opin. Immun.* 9:189–194), and most recently the neuropeptide galanin (Pooga, et. al., (1998) *FASEB J.* 12:67–77). Delivery of protein substrates has been demonstrated by some of these transport peptides as well (Phelan, et. al., (1998) *Nature Biotechnology* 16:440–443, Fawell, et. al., (1994) *Proc. Natl. Acad. Sci.* 91:664–668, Rojas, et. al., (1998) *Nature Biotechnology* 16:370–375).

Hsps also serve a number of key functions in the immune response, and over the past few years there has been increasing interest in characterizing the nature of Hsps in generating protective immunity. A series of recent studies (Román, et. al., (1996) *Immunology* 88:487–492, Suzue, et. al., (1996) *J. Immunol.* 156:873–879) demonstrated that Hsp70 could act as a carrier protein to enable a bound peptide or protein substrate to enter the endosomal compartment and subsequently access the MHC class II processing pathway for exogenous antigens. Such treatment with Hsp70-peptide complexes or Hsp70 fusion proteins could elicit cargo-specific proliferative T cell responses. However, other experiments in which cancer cell-derived Hsp70 used to immunize mice resulted in specific antitumor CTL responses (Udono, et al., (1993) *J. Exp. Med.* 178:1391–1396) suggested that the Hsps were using the endogenous MHC class I processing pathway. These data implied that Hsp70 was able to cross the plasma membrane and enter the cytoplasmic compartment of intact cells. Earlier studies (Hightower, et al. (1989) *J. Cell Physiol.* 138:257–266) reporting the release of Hsps from axonal cells by a non-heat shock dependent mechanism, support the observation that some Hsp family members can cross the plasma membranes of certain cells.

Although the above studies imply a plasma membrane translocation capacity for Hsp70, such an activity has not been directly demonstrated. It has not been shown whether or not Hsp70 could be utilized to deliver proteins across the plasma and nuclear membranes. There exists a need to deliver compounds, such as proteins or DNA, into the cell nucleus to modulate cellular activity.

Applicants have shown that the human 70 kD heat shock protein can translocate across cell membranes to rapidly gain cytoplasmic and nuclear entry. Furthermore, chimeric proteins composed of Hsp70 peptides fused to amino acids 37–409 of the p50 subunit of NF-κB (Meyer, R., et. al., PNAS 88:966–970 (1991); Genbank Accession No. M58603) also exhibit this translocation property. Though cellular import activity has been reported for various diverse peptides, intranuclear transport generally requires the presence of specific nuclear localization sequences ("NLS"). While heat shock is known to induce increased synthesis and nuclear translocation of endogenous heat shock protein following heat shock factor activation, Applicants show that nuclear localization of exogenous heat shock protein can result without prior heat shock. Applicants have also shown that the transport and nuclear localization properties of Hsp70 are retained within a 90 amino acid C-terminal fragment; successful intranuclear transport has been demonstrated utilizing a C-terminal fragment as well as larger fragments encompassing more of the peptide binding domain. Herein is the first evidence establishing the ability of exogenous Hsp70 fusion proteins to cross the cell membrane, gain nuclear entry and exert a biological function.

Therefore, an object of the present invention is to provide a carrier for delivery of molecules with biological function into both cellular and nuclear compartments. A preferred embodiment of the present invention utilizes Hsp70, or a fragment of Hsp70 as described herein, as a vehicle for directed, noninvasive delivery of molecules, such as proteins or DNA, that may modulate gene expression.

SUMMARY OF THE INVENTION

The 70 kD heat shock protein ("Hsp70") is a highly conserved, ubiquitous protein involved in chaperoning proteins to various cellular organelles. Applicants herein show that when added exogenously to cells, Hsp70 is readily imported into both cytoplasmic and nuclear compartments. Applicants have demonstrated that Hsp70 can be used to chaperone compounds into a cell or cells. Hsp70 was used to deliver NF-κB, a key transcriptional regulator of inflammatory responses, into the nuclear compartment. Applicants herein show that a fusion protein composed of a C-terminal Hsp70 peptide and amino acids 37–409 of the p50 subunit of NF-κB was directed into the nucleus of cells, could bind DNA specifically, and activated kappa Ig expression and TNFα production. Applicants' invention encompasses the use of Hsp70 as a vehicle for intracytoplasmic and intranuclear delivery of proteins or DNA to modulate gene expression and thereby control immune responses.

DESCRIPTION OF THE FIGURES

FIG. 1 shows various cell types that exhibit differential Hsp70 uptake activity. Various cells were treated with 10 μg/ml Hsp70-FITC added to the culture media. Human peripheral blood cells were stained with anti-CD14-PE as a marker for monocytic cells, anti-CD19-PE for B cells, or anti-CD3-PE for T cells. After one hour of incubation at 37° C., cells were washed in PBS, fixed in 2% paraformaldehyde, washed again and re-suspended in PBS for visualization by confocal laser scanning microscopy.

Equimolar amounts of BSA-FITC were used in parallel experiments as a control.

FIG. 2 shows the kinetics of Hsp70 cellular uptake.

FIG. 6 shows that internalized Hsp70-p50 fusion proteins exhibited DNA-binding activity. 70Z/3 cells were treated as indicated for one hour prior to lysis and generation of nuclear extracts. EMSA was performed and specific DNA binding complexes were identified by supershift assay with the indicated antibodies.

FIG. 7 shows that Hsp70-p50-treated cells became activated to express surface kappa Ig and produce TNFα.

DETAILED DESCRIPTION OF THE INVENTION

Figure 1A:
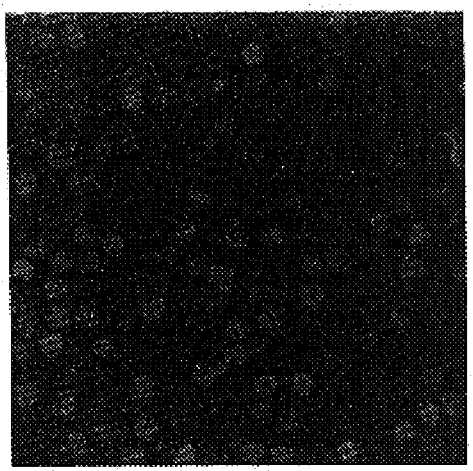
FIG. 1A shows 70Z/3 cells+Hsp70-FITC.

The present invention demonstrates that the heat shock protein Hsp70 is internalized by cells into both the cytoplasm and nucleus in a cell type specific manner. Although the mechanism of uptake is unknown, the data suggest that the binding and internalization of Hsp70 is energy dependent and involves a high capacity receptor.

The observation that cell surface-associated and secreted forms of Hsp70 exist (Multhoff, et al., (1996) *Cell Stress & Chaperones* 1:167–176) suggests that this protein may function in cell—cell communication, perhaps as a means of transferring cellular protection from environmental stressors by regulating transcription. In fact, several recent reports have described a physical interaction of Hsp70 with the transactivation domains of several transcription factors within the nucleus. For example, Hsp70 can bind directly to the transactivation domains of both HSF (heat shock factor) (Shi, et al., (1998) *Genes Dev.* 12:654–666), resulting in inhibition of gene transcription, and Wilms tumor suppressor (Maheswaran, et al., (1998) *Genes Dev.* 12:1108–1120), resulting in suppression of cellular proliferation. These data and others implicate a role for Hsp70 in the regulation of transcription factors and possibly other nuclear proteins. These data complement others which have shown that Hsp70 as a cytoplasmic chaperone can interact with transcription factors such as NF-κB itself, as well as a myriad cofactors such as Hip, Hop, Hsp40, Hsp90, BAG-1 and others (Demand, et al., (1998) *Mol. Cell. Biol.* 18:2023–2028). Indeed, release and intercellular transfer of exported Hsp70 has been reported in glial and axonal cells (Hightower, et al., (1989) *J. Cell Physiol.* 138:257–266); and accumulation of Hsp70 in a variety of human cell lines either by heat shock or by liposomal transfer has been shown to increase cell survival and protect from apoptotic cell death (Lasunskaia, et al., (1997) *Apoptosis* 2:156–163). Release of heat shock proteins from cells under harsh or damaging conditions may be a homeostatic mechanism for transfer of a protective stress response to neighboring cells that are unable to mount such a response. In addition, recent reports describing the ability of peptide-bound Hsp70 molecules to induce antitumor or antiviral immunity as well as development of memory CTLs support the notion that these proteins might function to convey a protective immune response by providing an antigen presentation function (Blachere, et al., (1997) *J. Exp. Med.* 186:1315–1322; Ciupitu, et al., (1998) *J. Exp. Med.* 187:685–691). Applicants submit that endogenous Hsp70 (and associated peptides or proteins) is/are released into the environment by infected or apoptosing cells. These Hsp70 protein complexes would subsequently become available to neighboring cells which may be compromised in their immune capacity, and act as a stimulus to boost or strengthen the immune response.

Applicants have demonstrated the efficient cellular and nuclear uptake as well as long-term intracellular stability of exogenously supplied Hsp70 fusion proteins by a variety of cell types. This rapid and stable transport activity has important implications for the utility of Hsp70-derived peptides as a vehicle for delivering therapeutic agents to the cytoplasm and nucleus where they remain localized for long periods of time. As manipulation of the nuclear import process in particular becomes an increasingly more interesting target for regulated control of gene expression (Fujihara, et al., (1998) *Biochem. Pharm.* 56:157–161), it is believed that future emphasis will be placed on developing more potent means of intracellular targeted delivery. The use of Hsp70 as a delivery system has a number of advantages over other previously described protein candidates, including the fact that the protein is of human origin and therefore does not contain foreign (i.e., viral or insect) and potentially immunogenic material. Use of soluble fragments of Hsp70 will potentially reduce immunogenicity further. As Hsp70 is a highly expressed abundant protein, it would likely be well-tolerated in humans, and in fact already plays an immune response role. In addition, the cell type-specificity we observed would allow the targeting of compounds to specific cells of the immune system for more effective regulatory control. And finally, the preferential and long-lived nuclear directed delivery of protein substrates may provide protection from cytoplasmic proteolysis. Our data support the potential use of Hsp70 sequences as a novel tool to deliver molecules that modulate gene expression and subsequently provide immunosuppressive or immunostimulatory control.

Applicants disclose in an embodiment of the present invention a fusion protein comprising a fragment of Hsp70 joined to amino acids 37–409 of the NF-κB p50 subunit (the fusion proteins are referred to herein as Hsp70-p50, Hsp70/28-p50, or Hsp70/10-p50). Although NF-κB p50 homodimers are commonly thought to act as NF-κB transcriptional repressors in most cell types due to the absence of a C-terminal activation domain, the downstream biological events Applicants observed did not reflect a dominant negative effect of the fusion protein on transcriptional activation. There are a number of possible explanations for the Hsp70-p50-induced transactivation observed. First, the heat shock protein sequence, specifically the EEVD domain, may itself contain transactivation activity. Hsp70 is known to bind heat shock factor in the nucleus and interfere with its transactivation activity via the EEVD domain. Since the Hsp70 sequence in the Examples below was cloned C-terminal to amino acids 37–409 of the NF-κB p50 sequence (SEQ ID NO:1), the EEVD domain is potentially available to provide transactivation, or even to interact with other cellular or nuclear cofactors. Amino acids 37–409 of the NFκB p50 sequence (SEQ ID NO:1), as shown in Meyer, R., et al., Natl. Acad. Sci., February 1991, Vol. 88, pp. 966–970, are:

LPTDGPYLQILEQPKQRGFRFRYVCEGP-
SHGGLPGASSEKNKKSYPQVKICNYV GPA-
KVIVQLVTNGKNIHLHAHSLVGKHCEDG-
ICTVTAGPKDMVVGFANLGILHVTK
KKVFETLEARMTEACIRGYNPGLLVHPD-
LAYLQAEGGGDRQLGDREKELIRQAAL QQT-
KEMDLSVVRLMFTAFLPDSTGSFTR-
RLEPVVSDAIYDSKAPNASNLKIVRMDR
TAGCVTGGEEIYLLCDKVQKDDIQIRFY-
EEEENGGVWEGFGDFSPTDVHRQFAIVF KTP-
KYKDINITKPASVFVQLRRKSDLETSEP-
KPFLYYPEIKDKEEVQRKRQKLMPNF
SDSFGGGSGAGAGGGGMFGSGGGGGTG-
STGPGYSFPHY.

Closer analysis of the nuclear complex may yield clues as to other possible components with transcriptional activities. Second, p50 homodimers may simply exhibit transactivation activity in particular circumstances. Fujita, et al. ((1992) *Genes Dev.* 6:775–787) tested the various homo- and heterodimers of NF-κB subunits for transcriptional activation in vitro and determined that addition of p50 alone to some transcription mixtures resulted in significant transcriptional stimulation. They attribute this activation to differences in the fine structure of the nucleotide sequence within the κB motifs. Interestingly, this group observed a four-fold stimulation of transcription by p50 homodimers over control using the Igκ sequence motif. These data would correspond to the activation we observed in studies analyzing surface kappa Ig expression. Third, the Hsp70-p50 subunits may be recruiting other transactivating factors into the DNA binding complex that we have not yet detected.

Therefore, the present invention encompasses the use of Hsp70, or a fragment of Hsp70, to modulate cellular activity, preferably modulate nuclear activity in a cell or cells, for example the activity of transcription factors. The term "nuclear activity" encompasses the transcription of nucleic acid molecules in the cell. The term "modulate" encompasses enhancement, diminishment, activation or inactivation of cellular activity. The Hsp70 protein or a fragment thereof may be used alone to modulate cellular activity by transfer into the cytoplasm and/or nucleus of a cell, to treat Hsp70-associated disorders. "Hsp70-associated disorders" refers to any disorder or disease state in which Hsp70 plays a regulatory role in the metabolic pathway of that disorder or disease. As used herein the term "treating" refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

Additionally, the present invention encompasses the use of Hsp70, or a fragment of Hsp70, as a chaperone to carry one or more compounds into a cell. Hsp70 or a fragment thereof is joined to a compound to form a complex (herein referred to as an "Hsp70 complex" which includes the Hsp70, or fragment thereof, and any compound associated with or joined to the Hsp70 protein or fragment thereof). The Hsp70 complex is then provided to a cell or cells, or to the environment surrounding a cell or cells, so that the Hsp70 complex is transported into the cytoplasm and/or nucleus of the cell or cells. Compounds that may be joined to the Hsp70 protein or a fragment thereof include, but are not limited to, proteins, peptides, nucleic acids, and small molecules. "Nucleic acids" or "polynucleotides" includes individual nucleotides as well as DNA and RNA sequences or fragments thereof.

Disease states which may be treated by Hsp70, fragments thereof, and/or Hsp70 complexes of the present invention include transplant rejection and autoimmune diseases, such as rheumatoid arthritis, multiple sclerosis, juvenile diabetes, asthma, and inflammatory bowel disease, as well as inflammatory diseases, cancer, viral replication diseases and vascular diseases.

For example, the Hsp70 complexes and pharmaceutical compositions of the present invention are useful in the treatment of transplant rejection (e.g., kidney, liver, heart, lung, pancreas (e.g., islet cells), bone marrow, cornea, small bowel and skin allografts, and heart valve xenografts) and autoimmune diseases, such as rheumatoid arthritis, multiple sclerosis, juvenile diabetes, asthma, inflammatory bowel disease (Crohn's disease, ulcerative colitus), lupus, diabetes, myasthenia gravis, psoriasis, dermatitis, eczema, seborrhoea, pulmonary inflammation, eye uveitis, hepatitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis, inflammatory diseases such as osteoarthritis, acute pancreatitis, chronic pancreatitis, asthma and adult respiratory distress syndrome, as well as in the treatment of cancer and tumors, such as solid tumors, lymphomas and leukemia, vascular diseases such as restenosis, stenosis and artherosclerosis, and DNA and RNA viral replication diseases, such as retroviral diseases, and herpes.

Also within the scope of the present invention are pharmaceutical compositions comprising at least one Hsp70 complex comprising a compound that is to be delivered to the cytoplasm and/or nucleus of a cell or cells. The Hsp70 complex may be administered alone or with at least one additional active compound, and any pharmaceutically acceptable carrier, adjuvant or vehicle. "Additional active compounds" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with an Hsp70 complex of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as dα-tocopherol polyethyleneglycol 1000 succinate, surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical compositions comprising at least one Hsp70 complex of the present invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions), nasally such as by inhalation spray, topically, such as in the form of a cream or ointment; or rectally such as in the form of suppositories; in dosage unit formulations containing non-toxic, pharmaceutically acceptable vehicles or diluents. The pharmaceutical compositions of the present invention may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present Hsp70 complexes may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art, and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present Hsc70 complexes with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

A "therapeutically effective" amount of an Hsp70 complex of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 3 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans.

By "therapeutically effective" is meant an amount necessary to achieve a desired result, for example, alleviation of symptoms of a particular disorder in a patient, the improvement of an ascertainable measurement associated with a particular disorder, or the prevention of a particular immune response. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans.

The Hsp70 complexes of the present invention may be employed alone or in combination with each other and/or other suitable therapeutic agents, such as antiinflammatories, antiproliferatives, chemotherapeutic agents, and immunosuppressants.

The following examples are meant to be illustrative of an embodiment of the present invention and do not limit the scope of the invention in any way. All references cited herein, whether supra or infra, are hereby incorporated by reference in their entirety.

Manufacture of Recombinant Hsp70

The following method was used to make recombinant Hsp70: Hsp70 fusion proteins were generated by PCR amplification of human Hsp70 DNA sequences using primers corresponding to the published sequence and including restriction endonuclease sites to enable directed cloning into a prokaryotic expression vector, ProExHta (Life Technologies, Inc.). NF-κB p50 sequences were generated in the same way, using primers corresponding to the published p50 sequence and cloned upstream of (5' to) Hsp70 sequences in the same expression vector. The cloning vector included a 6×His tag for use in purification of expressed protein over a metal column. DNA was transformed into a bacterial host and protein expression was induced using IPTG. Soluble, expressed fusion protein was purified using conventional affinity purification techniques and subsequently used for the following experiments.

EXAMPLE 1

Hsp70-mediated Transport is Cell-Type Specific

Figure 1B:
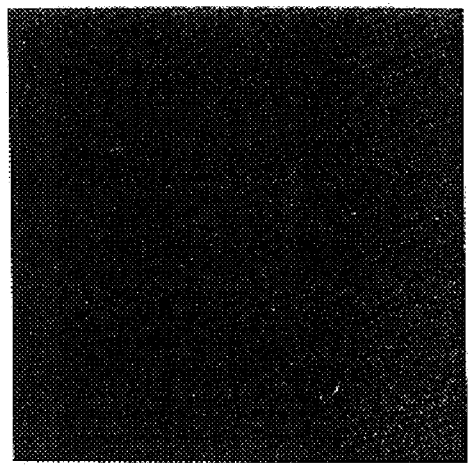
FIG. 1B shows 70Z/3 cells+BSA-FITC.
Figure 1C:
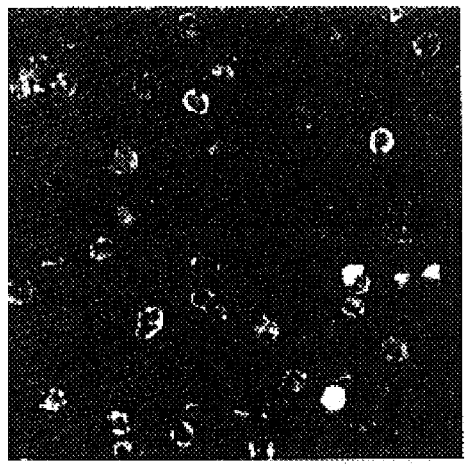
FIG. 1C shows PBL stained with anti-CD14-PE+Hsp70-FITC.
Figure 1D:
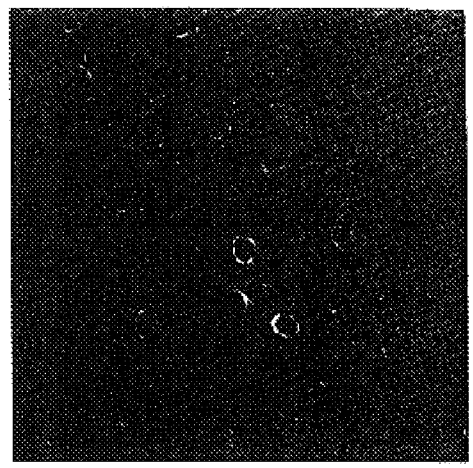
FIG. 1D shows PBL stained with anti-CD14-PE+BSA-FITC.
Figure 1E:
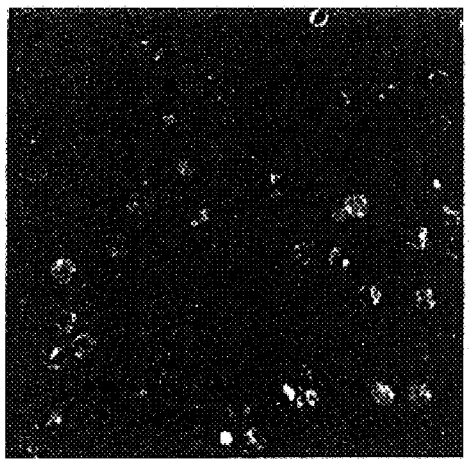
FIG. 1E shows PBL stained with anti-CD19-PE+Hsp70-FITC.
Figure 1F:
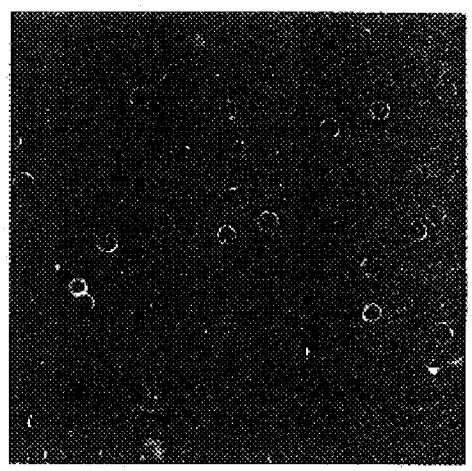
FIG. 1F shows peripheral blood T cells stained with anti-CD3-PE+Hsp70.

To investigate the intracellular localization of exogenously added Hsp70, we fluorescently labeled the full-length Hsp70 protein and tested its ability to become internalized by various cell types. Cells were treated with a final concentration of 10 μg/ml Hsp70-FITC (or BSA-FITC as a control) for 1 hour, then washed and fixed prior to confocal laser scanning microscopy. The bulk of the intracellular Hsp70-FITC localized uniformly to the nucleus and cytoplasm in murine pre-B 70Z/3 cells, whereas import of BSA-FITC was negligible (FIGS. 1A and 1B). We also observed significant uptake of Hsp70-FITC by human peripheral blood monocytes, but not T cells (FIGS. 1C–1F). Interestingly, while the staining pattern in peripheral blood monocytes was often uniform throughout the cytoplasm and nucleus, we noted that it was sometimes characterized by punctuate staining, implying vesicular localization within the cytoplasm. Applicants found that the specific staining pattern of the PBLs varied by donor, suggesting that the state of cell activation may play a role in uptake efficiency or intracellular localization of exogenous Hsp70. Consistent with this hypothesis, we found that while resting peripheral blood B cells were resistant to uptake, they could be induced to transport the protein after 48 hours of activation in vitro with anti-CD40 plus anti-Ig antibodies. This method of B cell activation is known to result in the expression of various differentiation and proliferation associated genes. In contrast, activation of peripheral blood T cells by anti-CD3 and anti-CD28 antibodies did not affect Hsp70 transport. No intracellular uptake was observed by Jurkat T cell line or HeLa fibroblast cell line, but we did observe efficient uptake by two mature B cell lines, RAJI and BJAB. In addition, we saw limited cytoplasmic uptake by two monocytic cell lines, THP-1 and U937, but only after extended (6 to 24 hours) incubation with high concentrations (100 μg/ml) of Hsp70-FITC. The B cell- and monocyte-specific Hsp70 transport activity we describe is consistent with reports which propose a role for Hsp70 heat shock family members in antigen presentation (Manara, et al., (1993) *Blood* 82:2865–2871; Vanbuskirk, et al., (1989) *J. Exp. Med.* 170:1799–1809) as these cells are generally considered to function as antigen presenting cells. The cell type specificity and inducibility of cellular Hsp70 uptake may reflect differential expression of a required surface or nuclear receptor for the Hsp70 protein. Studies are now in progress to investigate the surface proteins which may be involved in the binding and internalization of extracellular Hsp70.

EXAMPLE 2

Kinetics of Hsp70 Cellular Uptake

Figure 2A:
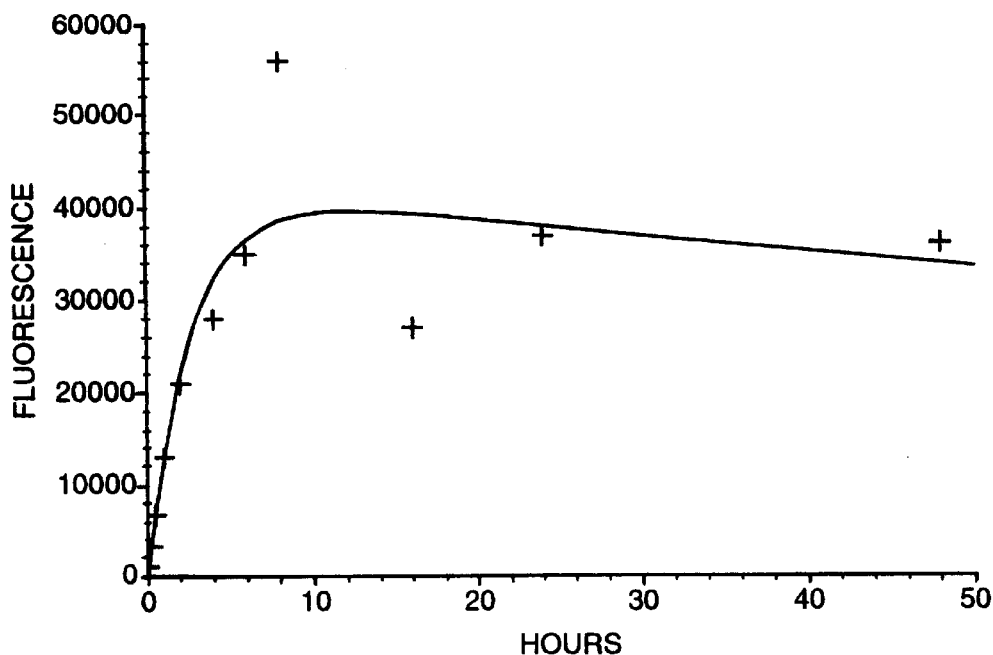
FIG. 2A shows the kinetics of uptake of Hsp70-FITC by 70Z/3 cells. The cells were incubated at 37° C. for various times with 1 $\mu$M Hsp70-FITC in complete RPMI. Cells were washed once in PBS to separate free Hsp70-FITC, then re-suspended in PBS and analyzed by fluorimeter. Points were experimental and the curve was fitted by a modified regression program (XL1fit).

We next investigated the time-course and dose effect of Hsp70 uptake by 70Z/3 cells. $5 \times 10^5$ cells were incubated at 37° C. with 1 μg/ml Hsp70-FITC for increasing periods of time from 10 minutes to 48 hours. After unincorporated Hsp70-FITC was washed away with PBS, intracellular and cell-associated fluorescence was quantified by fluorimeter analysis. From these studies we determined that the internalization process appears to be slow, since maximal internalization is not achieved until between 6–8 hours (FIG. 2A), after which time the rate of uptake appears to drop slightly and remain constant for up to 2 days of incubation.

Figure 2B:
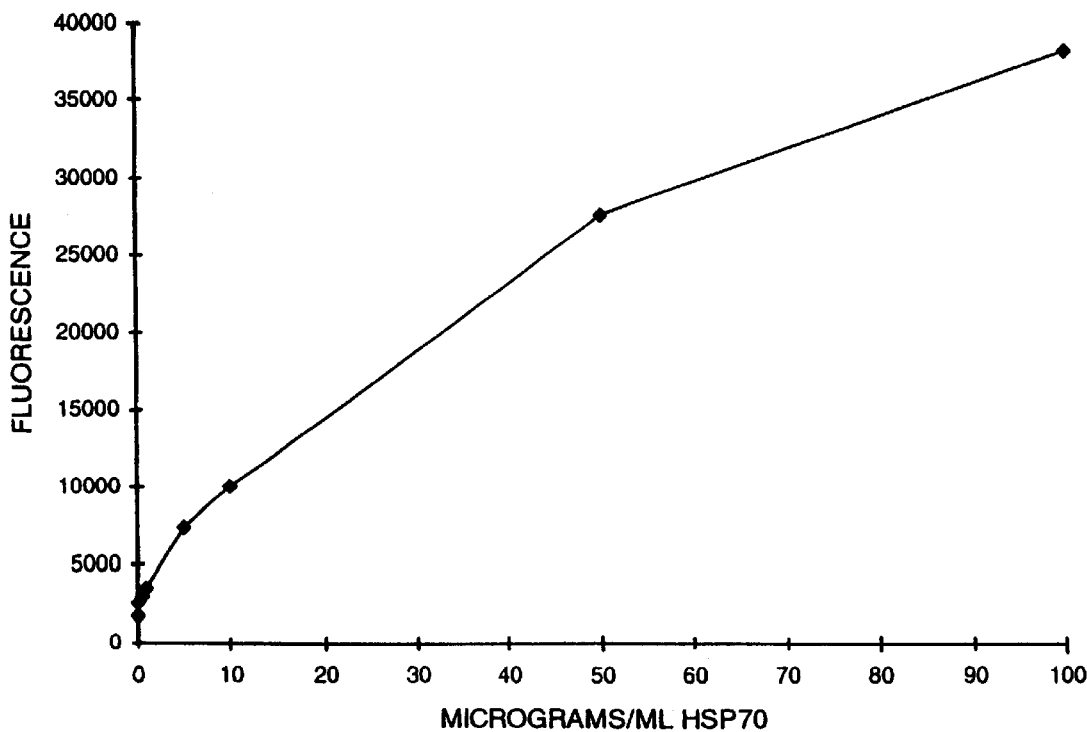
FIG. 2B shows the dose effect of Hsp70 on uptake by 70Z/3 cells. The cells were incubated at 37° C. for one hour with various concentrations of Hsp70-FITC, then washed and analyzed as in (A).

For the dose range study we chose a one-hour incubation time and treated cells with varying amounts of Hsp70-FITC. Our analysis showed that the intensity of intracellular fluorescence increased with increasing concentrations of extracellular Hsp70, up to 100 μg/ml (1.4 μM), and was detectable even when cells were treated with levels as low as 0.1 μg/ml (1.4 nM, FIG. 2B). We determined that treatment of cells with an extracellular concentration of 1 μM Hsp70-FITC resulted after one hour of incubation in an intracellular concentration of 700 nM, assuming a volume of 1 pl/cell. This uptake efficiency is comparable to that reported for other peptide sequences (Phelan, et al., (1998) *Nature Biotechnology* 16:440–443). The uptake of Hsp70-FITC was not saturable in the concentration range we used (35 nM-1 μM), indicative of a high capacity receptor-mediated uptake mechanism. In addition, internalization could not be blocked by preincubation with a 10-fold excess of unlabeled Hsp70.

EXAMPLE 3

Mechanism of Hsp70-Mediated Intracellular Transport

Figure 3A:
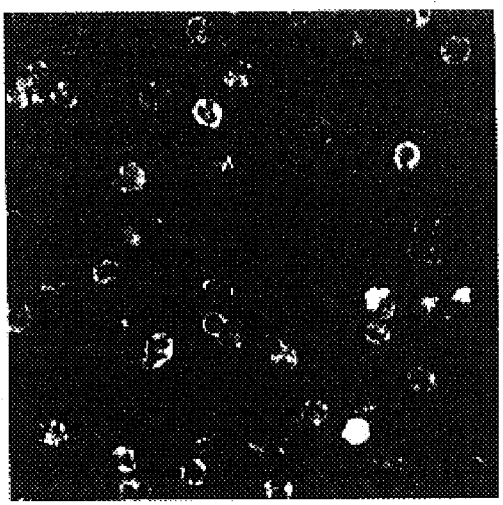
FIG. 3 shows that intracellular uptake of Hsp70-FITC was not affected by azide but was inhibited at 4° C. 70Z/3 cells were either untreated (FIG. 3A) or pretreated for 30 minutes with 0.05% sodium azide (FIG. 3B) before incubation with Hsp70-FITC at 37° C., or were preincubated at 4° C. for 30 minutes prior to addition of Hsp70-FITC and an additional one hour of incubation at 4° C.
(FIG. 3C). BSA-FITC was added to cells for 1 hour at 37° C. as a control (FIG. 3D). Internalized Hsp70-FITC did not co-localize with transferrin. Cells were treated with both Hsp70-FITC and Texas Red-conjugated transferrin, for one hour at 37° C.
(FIG. 3E).
Figure 3C:
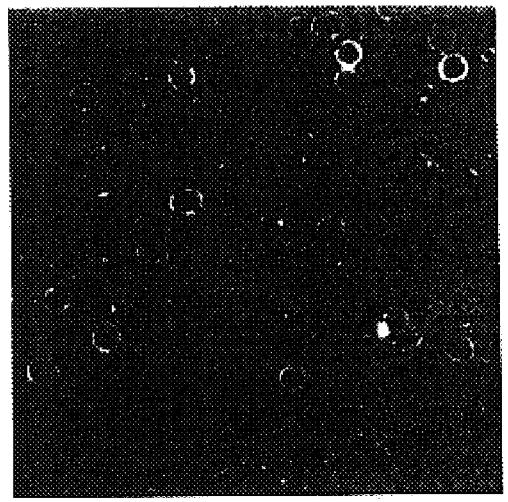
Figure 3B:
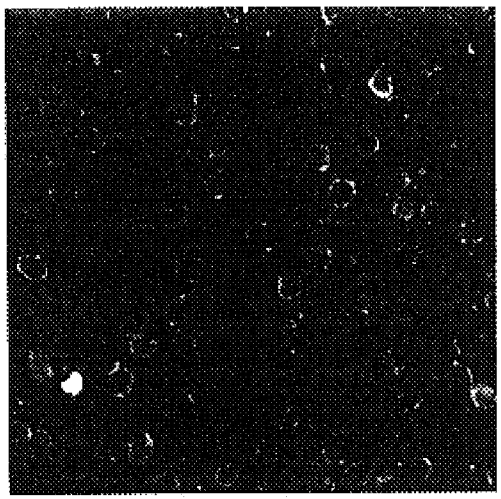
Figure 3D:
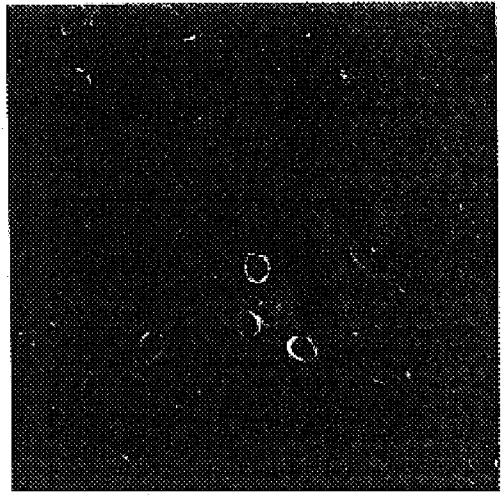
Figure 3E:
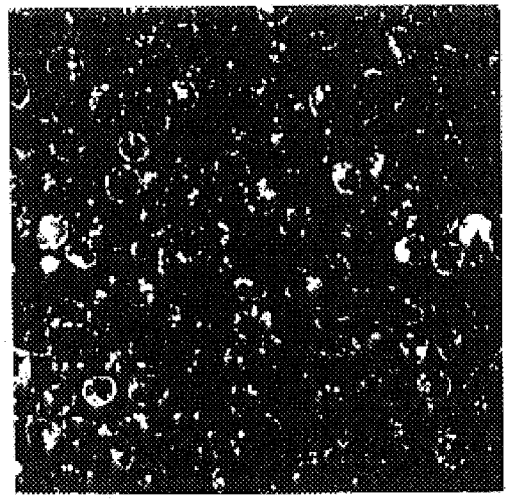
Figure 4A:
FIG. 4 shows transport of fusion proteins into the cytoplasm and nucleus. FITC-labeled fusion proteins consisting of either the C terminal 244 (Hsp70/28-p50) or 92 (Hsp70/10-p50) amino acids of Hsp70, fused to amino acids 37–409 of the p50 subunit of NF-κB, were transported into 70Z/3 cells. 70Z/3 cells were treated with full-length Hsp70-FITC (FIG. 4A), Hsp70/28-p50-FITC (FIG. 4B), Hsp70/10-p50-FITC (FIG. 4C), or BSA-FITC as a control (FIG. 4D) for 1 hour at 37° C. as described. Intracellular localization of fusion proteins was visualized by confocal laser scanning microscopy.
Figure 4C:
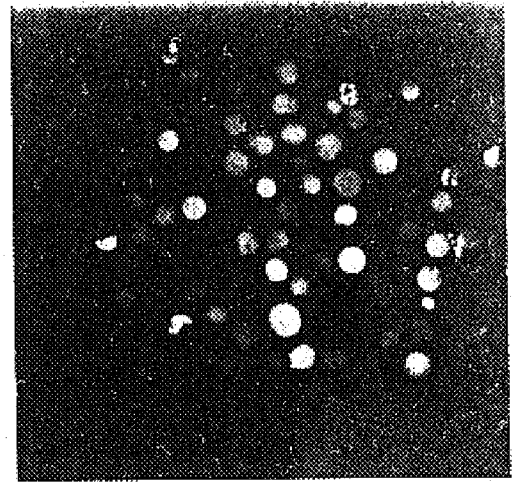
Figure 4B:
Figure 4D:
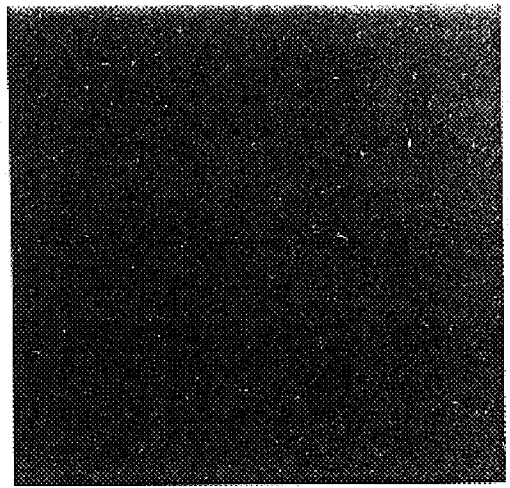

To investigate the mechanism of transport, we examined the import of Hsp70 under various conditions. Although full-length Hsp70 protein was transported by PBLs in the presence of 0.05% sodium azide, this transport activity was completely eradicated when cells were incubated at 4° C. (FIGS. 3A–3D), suggesting that there is an energy-dependent component to the Hsp70-mediated transport. These data coupled with co-internalization studies using transferrin, which revealed that accumulation of transferrin and Hsp70 occurred in separate intracellular compartments in both 70Z/3 cells (FIG. 3E) and in human PBLs, suggested that this mechanism does not involve classical endocytosis.

EXAMPLE 4

An Exogenous NF-κB-C terminal Hsp70 Fusion Protein Can Be Directed to the Nucleus Two different fusion proteins composed of either a 244 (SEQ ID NO:2) or a 92 (SEQ ID NO:3) amino acid Hsp70 C-terminal polypeptide fused to the p50 subunit of the transcription factor NF-κB were generated to examine the ability of the Hsp70 peptide sequence to direct other protein substrates into the cell. The 244 amino acid polypeptide has the following sequence:

```
PLSLGLETAG GVMTALIKRN STIPTKQTQI FTTYSDNQPG

VLIQVYEGER AMTKDNNLLG RFELSGIPPA PRGVPQIEVT

FDIDANGILN VTATDKSTGK ANKITITNDK GRLSKEEIER

MVQEAEKYKA EDEVQRERVS AKNALESYAF NMKSAVEDEG

LKGKISEADK KKVLDKCQEV ISWLDANTLA EKDEFEHKRK

ELEQVCNPII SGLYQGAGGP GPGGFGAQGP KGGSGSGPTI EEVD
```

The 92 amino acid polypeptide has the following sequence:

```
KSAVEDEGLK GKISEADKKK VLDKCQEVIS WLDANTLAEK

DEFEHKRKEL EQVCNPIISG LYQGAGGPGP GGFGAQGPKG

GSGSGPTIEE VD
```

Figure 5A:
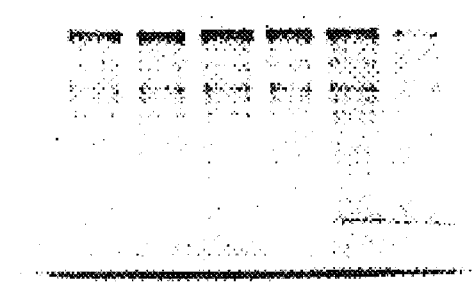
FIG. 5 demonstrates that internalized intracellular Hsp70 or Hsp70-p50 remained stable for up to 24 hours. Cells were treated with either full-length Hsp70-FITC (FIG. 5A) or Hsp70/28-p50-FITC (FIG. 5B) for one hour prior to washing and additional incubation at 37° C. for increasing times. Cells were harvested at the indicated timepoints, lysed in Laemmli sample buffer, and whole cell lysate proteins were separated by SDS-PAGE. Gels were subjected to fluorimager analysis. Lanes 1: cells untreated; lane 2: no chase; lane 3: 1 hour of chase; lane 4: 2 hours of chase; lane 5: 6 hours of chase; lane 6: 24 hours of chase; lane 7: 4 days of chase.
Figure 5B:
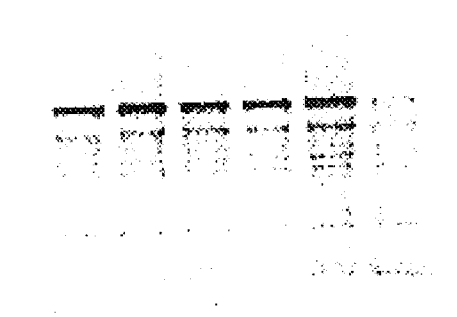

When added exogenously to cells, both FITC-conjugated fusion proteins entered the cytoplasm and nuclei of 70Z/3 cells (FIG. 4) and PBLs (data not shown) with kinetics and specificity similar to the Hsp70 peptide alone. This transport was stable, nonsaturable and occurred without significant protein degradation. Maximal uptake of FITC-Hsp70 remained stable after a 30 minute pulse for 24 hours after washout of unincorporated protein and incubation at 37° C., as determined by confocal microscopy and SDS-PAGE analysis. To assess protein stability, cells were pulsed with either 10 μg/ml FITC-conjugated full-length Hsp70 or Hsp70/28-p50 for 1 hour prior to washing and a chase at 37° C. for up to 96 hours. Whole cell extracts were generated by lysis in Laemmli sample buffer, and proteins were separated by SDS-PAGE. Gels were subjected to analysis by fluorimager, and results showed the presence of both the ~75 kD fusion protein as well as full-length Hsp70 itself (distinguishable from endogenous Hsp70 by its fluorescent tag) in whole cell extracts after up to 24 hours of incubation without measurable change in size or appearance of smaller molecular weight degradation products (FIG. 5). These data suggest that intracellular targeted Hsp70 was retained by the cell without significant degradation with a half-life of greater than 48 hours.

EXAMPLE 5

Transported NF-κB p50 Exhibits DNA-Binding Activity

Figure 6A:
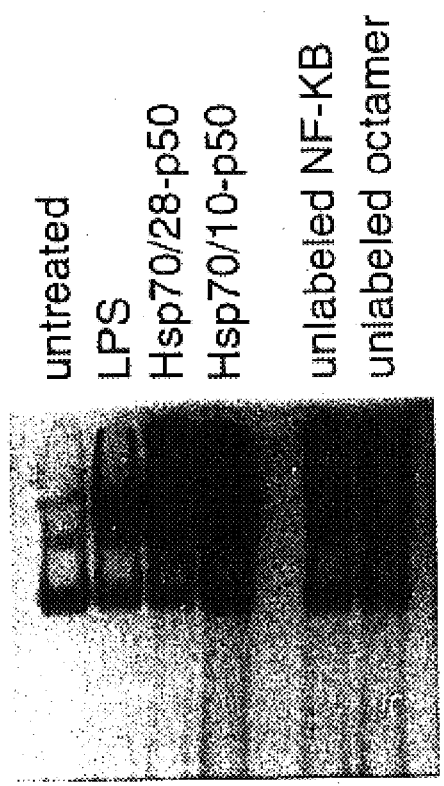
FIG. 6A, lane 1: unstimulated cells control; lane 2: LPS-treated; lane 3: Hsp70-p50-treated; lane 4: Hsp70-p50-treated extracts competed with unlabelled NF-κB oligo; lane 5: same as lane 4 but competed with unlabelled octamer oligo.
Figure 6B:
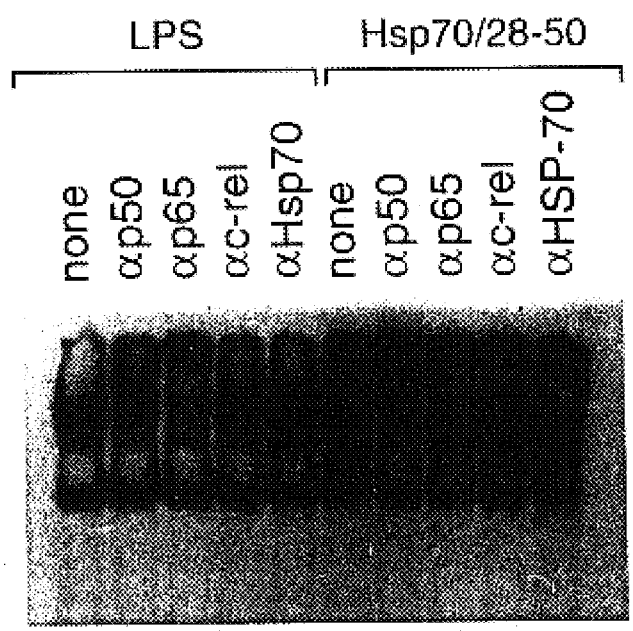
FIG. 6B, lane 1: LPS-treated; lane 2: LPS-treated and supershifted with anti-p50; lane 3: anti-p65; lane 4: anti-c-rel; lane 5: anti-Hsp70; Lanes 6–10, same as lanes 1–5 but using Hsp70-p50 treated extracts.

To address whether the internalized fusion proteins retained functional activity, we tested nuclear extracts of Hsp70-p50 fusion protein-treated cells for their ability to bind a specific kappa DNA sequence. We could show that purified fusion proteins were able to bind kappa DNA (data not shown), suggesting that the p50 subunits were not conformationally impaired by the presence of the Hsp70 sequences. After 70Z/3 cells were treated with 100 ng/ml LPS, 10 μg/ml Hsp70/10-p50 or Hsp70/28-p50 for 1 hour, nuclear extracts were prepared and gel shift assays were performed. We found that DNA binding activity was retained by the fusion protein after nuclear uptake by cells, indicating that the import process did not result in significant degradation or loss of activity (FIG. 6A). This DNA binding activity was specific, as the complex was competed with an excess of unlabeled NF-κB sequence but not with octamer sequence (FIG. 6A). We saw distinct complexes formed by nuclear extracts from cells treated with different fusion proteins; furthermore, they differed from the complex formed by LPS-induced endogenous NF-κB. In supershift experiments we observed that anti-p50 antibodies were able to shift nearly the entire DNA-binding complex from fusion protein-treated cells, as expected, confirming that the fusion protein was likely binding to DNA mainly as a homodimer (FIG. 6B). We also observed a detectable decrease in the specific complex upon incubation with both anti-p65 and anti-Hsp70 (directed against the carboxy-terminal four amino acids EEVD) antibodies, indicating the presence of endogenous p65 subunits in addition to recombinant Hsp70-p50 subunits. In contrast, nuclear extracts from control LPS-treated cells formed a complex containing both p50 and p65 subunits, and the supershifted patterns differed from the cells treated with the fusion protein. These data indicate that distinct protein/DNA complexes were formed and suggest that the fusion proteins were binding DNA directly and not simply activating endogenous NF-κB.

EXAMPLE 6

Figure 7A:
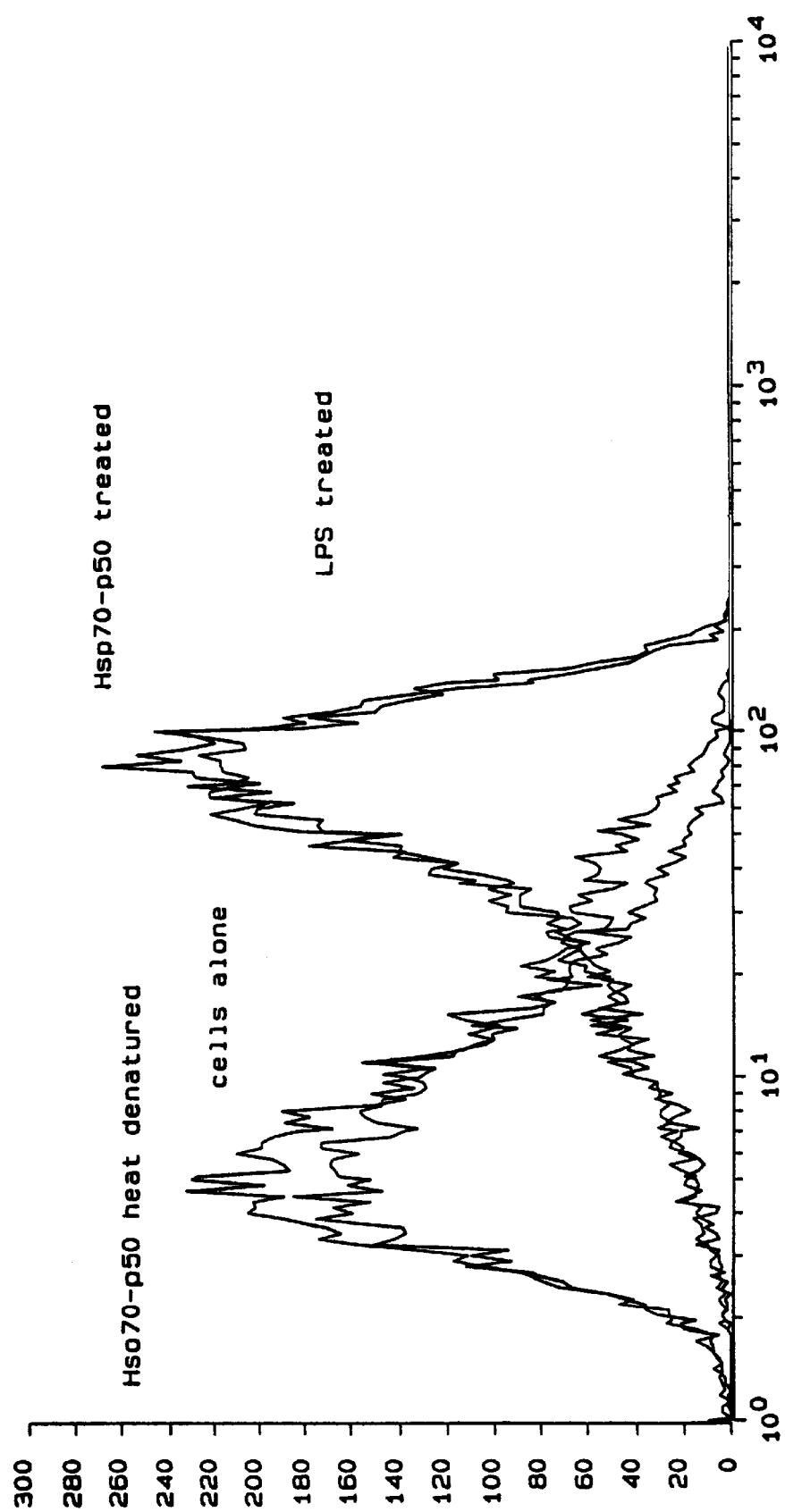
(FIG. 7A) 70Z/3 cells were treated with 10 ng/ml LPS or 30 $\mu$g/ml Hsp70/10-p50 overnight prior to washing and staining with anti-kappa-FITC and FACS analysis.
Figure 7B:
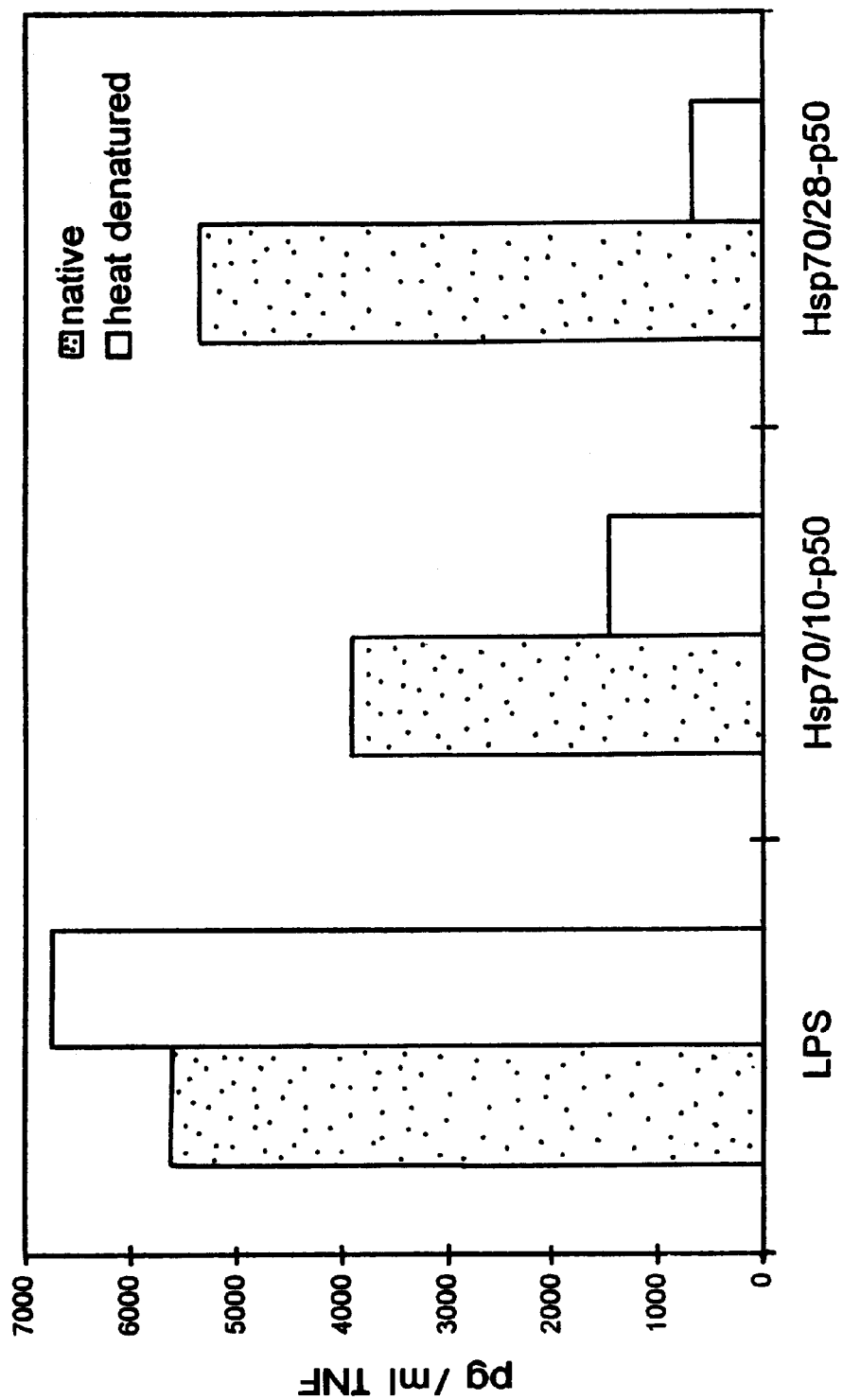
(FIG. 7B) Human peripheral blood lymphocytes were treated with 5 ng/ml LPS or 40 $\mu$g/ml Hsp70/10-p50 or Hsp70/28-p50 for 6 hours, and supernatants were harvested and analyzed for TNFα levels by ELISA.

Hsp70-p50 Fusion Protein Activates Surface kappa Ig Expression and TNFα Production Since treatment of cells with Hsp70-p50 fusion proteins could potentially result in the formation of complexes which interact with NF-κB DNA binding sites in cells, we decided to evaluate downstream biological events in the NF-κB pathway. We observed that treatment of various cells with the Hsp70-p50 fusion proteins resulted in activation of several inflammatory and immunological responses normally regulated by NF-κB. Treatment of mouse 70Z/3 pre-B cells with Hsp70/10-p50 fusion protein was shown to be as effective as LPS in inducing high levels of kappa Ig light chain on the surface (FIG. 7A). In addition, in contrast to LPS-induced activation, the fusion protein-induced surface kappa expression was abolished by 30 minutes of 65° C. heat denaturation of the protein prior to treatment of cells, confirming that intact protein was required for the activation. Similar results were obtained with Hsp70/28-p50 (data not shown). TNFα production is another example of an inflammatory response also largely regulated by NF-κB. We observed that the internalized fusion protein was also able to induce TNFα production by human peripheral blood lymphocytes (FIG. 7B). Freshly isolated PBLs were incubated with LPS or Hsp70-p50 for 6 hours, after which time supernatants were collected and tested for cytokine levels by ELISA. Again, we found the fusion proteins to be as effective as LPS in inducing TNFα production, and established that intact protein was responsible for activation by showing that heat denaturation of the fusion protein abolished the effect.

The following experimental procedures were used in the above examples:

Expression and purification of the Hsp70-p50 fusion proteins. Two p50 fusion proteins were constructed using the nucleotide sequence corresponding to amino acids 1–406 of the NF-κB p105 subunit protein. This sequence includes the DNA binding domain as well as the rel homology domain. The two fusion proteins varied in the length of Hsp70 fragment used. The two Hsp70 sequences were both derived from the C-terminus, including either the terminal 276 or 735 nucleotides, which correspond to a 10 kD (the 92 amino acid polypeptide discussed above) and a 28 kD (the 244 amino acid polypeptide discussed above) protein fragment. Either the 10 kD or the 28 kD Hsp70 protein was fused C-terminal to the p50 protein, and the resulting fusion proteins were denoted Hsp70/10-p50 or Hsp70/28-p50, respectively. The prokaryotic expression vector ProEX HT (Life Technologies, Gaithersburg, Md.) was used for cloning, expression and purification, as per the manufacturer's recommendations.

Confocal laser scanning microscopy. Cells were typically treated with 10 μg/ml FITC-conjugated proteins or as indicated in the text for one hour at 37° C. followed by a wash in PBS, fixation in 2% paraformaldehyde, an additional wash in PBS and subsequent visual analysis by confocal microscopy (Bio-Rad, Hercules, Calif.) using Molecular Dynamics LaserSharp software and Adobe Photoshop.

Western blot analysis of imported Hsp70-p50 fusion proteins. Cells were treated with FITC-conjugated proteins for one hour at 37° C., washed in PBS and used for preparation of nuclear extracts. Equal protein amounts were separated by SDS-PAGE. The gel was fixed in acetic acid and subject to fluorescence analysis by fluorimager and ImageQuant software.

Electrophoretic mobility shift assay. Nuclear extracts from 70Z/3 cells were prepared using a modification of established protocols (Tepper, et al., (1995) *J. Immunol.* 155:2427–2436). Protein concentrations were determined using the Bradford assay, and NF-κB (5'GATCCGAGGGGACTTTCCGCTGGGGACTTTCCA G3' (SEQ ID NO:4)) or octamer (5'TGTCGAATGCAAATCACTAGAA3' (SEQ ID NO:5)) oligonucleotides (Promega, Madison, Wis.) were end labeled with [γ-$^{32}$P]ATP and T4 kinase. The conditions for binding reactions with oligonucleotide probes were as previously described. Supershift assays were performed with NF-κB p50, p65 and c-Rel polyclonal antibodies (Santa Cruz Biotechnology, Santa Cruz, Calif.) and Hsp70 antibody by preincubating the nuclear extracts with 3 μl of the antibody in the reaction buffer for 30 minutes and continuing with the gel retardation assay according to standard procedures. Competition experiments were performed using unlabeled NF-κB and octamer oligonucleotides. Samples were analyzed on native 6% polyacrylamide gels and autoradiographed.

Immunofluorescence assay (FACS). 70Z/3 cells were treated with either 30 μg/ml Hsp70/10-p50 fusion protein or 100 ng/ml LPS and incubated overnight at 37° C. Cells were then washed in PBS and fixed in 2% paraformaldehyde prior to staining with FITC-conjugated anti-kappa antibody. After an additional PBS wash, cells were subjected to imaging and analysis on the FACSTAR.

TNFα assay. Human peripheral blood lymphocytes were isolated as previously described and treated with 40 μg/ml Hsp70 fusion protein or LPS for 6 hours. Supernatants were collected and analyzed for TNFα by ELISA (Genzyme, Cambridge, Mass.).

Although the present invention has been described in some detail by way of illustration and example for purposes of clarity and understanding, it will be apparent that certain changes and modifications may be practiced within the scope of the appended claims.

We claim:

1. A method for delivering a compound into a cell or cells, said method comprising:
   covalently joining said compound with Hsp70, or a fragment of Hsp70 capable of intracellular and intranuclear transport, to form an Hsp70 complex, and
   exogenously providing said Hsp70 complex to said cell or cells so that said Hsp70 complex is imported into said cell or cells,
   wherein said compound is a nuclear protein or nuclear peptide.

2. The method of claim 1 wherein said compound is capable of modulating activity in the nuclear compartment of said cell or cells.

3. A method of delivering a nuclear protein or nuclear peptide to the nuclear compartment of a cell or cells, said method comprising:
   covalently joining said nuclear protein or nuclear peptide with Hsp70, or a fragment of Hsp70 capable of intracellular and intranuclear transport, to form an Hsp70 complex, and
   exogenously providing said complex to said cell or cells so that said complex is transported into the nuclear compartment of said cell or cells.

4. The method of claim 3 wherein said Hsp70 complex is a fusion protein and said Hsp70 or fragment of Hsp70 comprises an amino acid sequence as shown in SEQ ID NO:2.

5. The method of claim 3 wherein said Hsp70 complex is a fusion protein and said Hsp70 or fragment of Hsp70 comprises an amino acid sequence as shown in SEQ ID NO:3.

6. The method of claim 5 wherein said nuclear protein or nuclear peptide comprises residues 37–409 of the p50 subunit of the transcription factor NF-κB as shown in SEQ ID NO:1.

7. A pharmaceutical composition comprising an Hsp70 complex, said Hsp70 complex comprising a first portion and a second portion covalently joined,
   said first portion comprising Hsp70 protein, or a fragment thereof capable of intracellular and intranuclear transport; and
   said second portion comprising a nuclear protein or nuclear peptide.

8. The pharmaceutical composition of claim 7 wherein said nuclear protein or nuclear peptide comprises the p50 subunit of the transcription factor NF-κB.

9. The pharmaceutical composition of claim 7 wherein said Hsp70 complex is a fusion protein.

10. The method of claim 4, wherein said Hsp70 or fragment of Hsp70 is the fragment of Hsp70 consisting of the amino acid sequence shown in SEQ ID NO:2.

11. The method of claim 5, wherein said Hsp70 or fragment of Hsp70 is the fragment of Hsp70 consisting of the amino acid sequence shown in SEQ ID NO:3.

12. The pharmaceutical composition of claim 9 further comprising at least one additional active compound selected from the group consisting of: an immunosuppressant, an anti-cancer agent, an anti-viral agent, an anti-inflammatory agent, an anti-fungal agent, an antibiotic, or an anti-vascular hyperproliferation compound.

13. The pharmaceutical composition of claim 9 wherein said Hsp70 or fragment of Hsp70 comprises an amino acid sequence as shown in SEQ ID NO:2.

14. The pharmaceutical composition of claim 9 wherein said Hsp70 or fragment of Hsp70 comprises an amino acid sequence as shown in SEQ ID NO:3.

15. The pharmaceutical composition of claim 13 or 14 wherein Hsp70 or fragment of Hsp70 is C-terminal to said nuclear protein or nuclear peptide.

16. The pharmaceutical composition of claim 7 wherein said nuclear protein or nuclear peptide comprises residues 37–409 of the p50 subunit of the transcription factor NF-κB as shown in SEQ ID NO:1.

17. A method of delivering a compound into a cell or cells, said method comprising:
   associating said compound with Hsp70, or a fragment of Hsp70 capable of intracellular and intranuclear transport, to form an Hsp70 complex; and
   providing said Hsp70 complex to said cell or cells or to the environment surrounding said cell or cells so that said Hsp70 complex is imported into said cell or cells;
   wherein said compound comprises residues 37–409 of the p50 subunit of the transcription factor NF-κB as shown in SEQ ID NO:1.

18. The method of claim 1, wherein said nuclear protein or nuclear peptide is covalently joined to a fragment of Hsp70 capable of intracellular and intranuclear transport.

19. The method of claim 1, wherein said Hsp70 or fragment of Hsp70 is of human origin.

20. The method of claim 1, wherein said nuclear protein or nuclear peptide is capable of modulating gene expression in said nuclear compartment.

21. The method of claim 20, wherein said modulation of gene expression provides immunosuppressive or immunostimulatory control.

22. The method of claim 20, wherein said nuclear protein or nuclear peptide is a transcription factor.

23. The method of claim 22, wherein said transcription factor is a regulator of inflammatory responses.

24. A pharmaceutical composition comprising an Hsp70 complex, said Hsp70 complex comprising a first portion and a second portion covalently joined,
   said first portion comprising Hsp70 of human origin, or a fragment of Hsp70 of human origin capable of intracellular and intranuclear transport, and
   said second portion comprising a nuclear protein or nuclear peptide.

25. The pharmaceutical composition of claim 7, wherein said nuclear protein or nuclear peptide is capable of modulating gene expression in said nuclear compartment.

26. The pharmaceutical composition of claim 25, wherein said modulation of gene expression provides immunosuppressive or immunostimulatory control.

27. The pharmaceutical composition of claim 25, wherein said nuclear protein or nuclear peptide is a transcription factor.

28. The pharmaceutical composition of claim 27, wherein said transcription factor is a regulator of inflammatory responses.

29. The pharmaceutical composition of claim 9, wherein said first portion consists of an amino acid sequence as shown in SEQ ID NO:2 or SEQ ID NO:3.

30. The pharmaceutical composition of claim 9, wherein said first portion consists of a fragment of Hsp70 protein capable of intracellular and intranuclear transport.

31. The pharmaceutical composition of claim 14, wherein said nuclear protein or nuclear peptide is a transcription factor.

32. A method of treating a disease in a patient comprising administering to said patient a therapeutically effective amount of a pharmaceutical composition according to claim 7, 9, 12, 13, 14, 16, 25, 27 or 31.

33. The method of claim 32, wherein the pharmaceutical composition is according to claim 31 and the patient is human.

34. A method of treating a disease in a patient comprising administering to said patient a therapeutically effective amount of a pharmaceutical composition according to claim 7, 9, 12, 13, 14, 16, 17, 25, 27, 29 or 30 wherein said disease is transplant rejection, an autoimmune disease, an inflammatory disease, cancer, a viral replication disease, or a vascular disease.

35. The method of claim 34 wherein said disease is transplant rejection, an autoimmune disease, an inflammatory disease or a vascular disease.

* * * * *